(12) United States Patent
Bak

(10) Patent No.: US 7,458,118 B2
(45) Date of Patent: Dec. 2, 2008

(54) PATIENT BED HAVING A DOCKING COLLIMATOR ASSEMBLY

(75) Inventor: Donald Bak, Streamwood, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 295 days.

(21) Appl. No.: 11/411,525

(22) Filed: Apr. 26, 2006

(65) Prior Publication Data

US 2008/0067457 A1     Mar. 20, 2008

(51) Int. Cl.
    *A61B 6/04* (2006.01)
(52) U.S. Cl. ................... 5/601; 5/611; 378/209
(58) Field of Classification Search ........ 5/601, 5/611; 378/209
    See application file for complete search history.

(56) References Cited

U.S. PATENT DOCUMENTS

| 4,131,801 | A | * | 12/1978 | Hogan | 5/601 |
| 4,490,835 | A | * | 12/1984 | Wons | 378/146 |
| 4,961,208 | A | * | 10/1990 | Okada | 378/18 |
| 5,105,086 | A | * | 4/1992 | Pierfitte et al. | 250/363.08 |
| 6,560,310 | B2 | * | 5/2003 | Stark | 378/37 |
| 7,254,851 | B2 | * | 8/2007 | Salit et al. | 5/601 |

* cited by examiner

*Primary Examiner*—Michael Trettel

(57) ABSTRACT

A patient bed is provided having an elevation mechanism resting on a platform and a collimator assembly, where the weight of the collimator assembly is selectively supported by one of the combination of the elevation mechanism and the platform when there is no patient laying on a mattress of the patient bed, and the platform alone when there is a patient laying on the mattress of the patient bed. The patient bed further includes first and second docking assemblies respectively mounted to a bed frame and the platform for docking the collimator assembly. The docking assemblies include self-aligning guide pins for maintaining a horizontal position of the collimator assembly and its collimators therein during docking and post-docking.

22 Claims, 3 Drawing Sheets

PATIENT BED HAVING A DOCKING COLLIMATOR ASSEMBLY

BACKGROUND

The present disclosure relates to a patient bed. Particularly, the present disclosure relates to a patient bed having a docking collimator assembly.

Technical Field

One type of patient bed includes a collimator assembly having several collimators for use in x-ray and gamma ray imaging. During imaging, one of the collimators is selected for filtering a stream of photons so that only those traveling parallel to a specified direction are allowed through for producing a readable image on a plate.

The collimator assembly is fixedly supported by a bed frame of the patient bed. The bed frame supports a mattress provided therein. Additionally, the bed frame is operatively connected to an elevation mechanism for raising and lowering the bed frame. The elevation mechanism is fixed to a platform or base of the patient bed and includes supports, bearings and motors for raising and lowering the bed frame. The components of the elevation mechanism are adapted to support the weight of a patient laying on the mattress, as well as the weight of the collimator assembly fixedly supported by the bed frame and the full compliment of collimators within the collimator assembly.

During a patient examination procedure of a patient laying on the mattress, the collimators of the collimator assembly are not accessed or needed. When there is no patient laying on the mattress, one or more collimators of the collimator assembly are accessed for observation and/or maintenance.

Thus, there exists a need to provide a patient bed having an elevation mechanism resting on a platform and a collimator assembly, where the weight of the collimator assembly is selectively supported by one of the combination of the elevation mechanism and the platform when there is no patient laying on a mattress of the patient bed, and the platform alone when there is a patient laying on the mattress of the patient bed. Such a patient bed does not require an elevation mechanism adapted to support the weight of the patient resting on the mattress, as well as the weight of the collimator assembly fixedly supported by the bed frame and the full compliment of collimators within the collimator assembly.

SUMMARY

The present disclosure relates generally to a patient bed having an elevation mechanism resting on a platform and a collimator assembly, where the weight of the collimator assembly is selectively supported by one of the combination of the elevation mechanism and the platform when there is no patient laying on a mattress of the patient bed, and the platform alone when there is a patient laying on the mattress of the patient bed. The patient bed further includes first and second docking assemblies respectively mounted to a bed frame and the platform for docking the collimator assembly. The docking assemblies include self-aligning guide pins for maintaining a horizontal position of the collimator assembly and its collimators therein during docking and post-docking.

DETAILED DESCRIPTION OF THE EXEMPLARY EMBODIMENT

Figure 1:
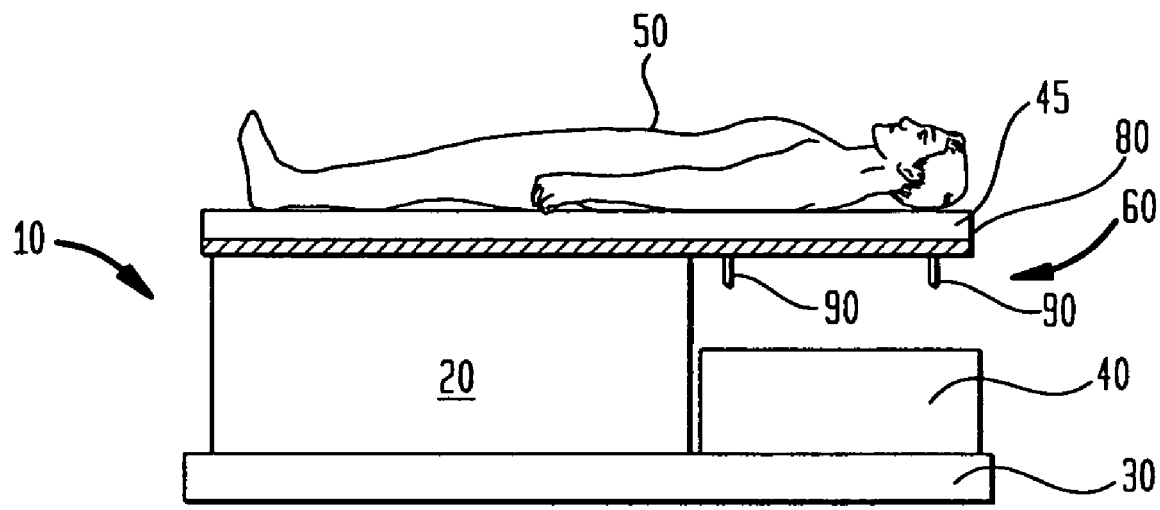
FIG. 1 is a schematic, cross sectional view of a patient bed where the collimator assembly is docked to a platform of the patient bed in accordance with an embodiment of the present invention.
Figure 2:
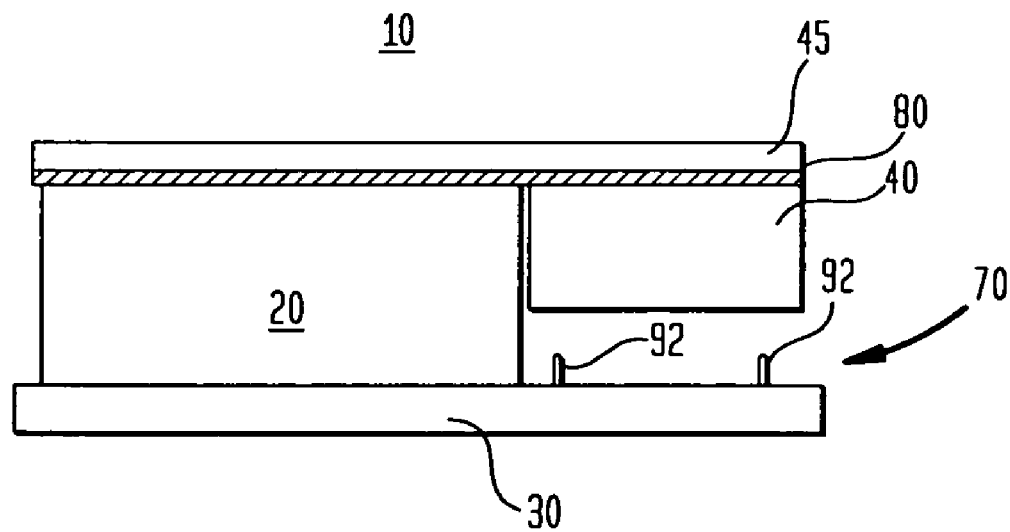
FIG. 2 is a schematic, cross-sectional view of the patient bed where the collimator assembly is docked to a bed frame of the patient bed in accordance with an embodiment of the present invention.

Turning to FIGS. 1 and 2 therein is shown an exemplary embodiment of the presently disclosed patient bed 10 having an elevation mechanism 20 resting on a base or platform 30 and a collimator assembly 40. The weight of the collimator assembly 40 is selectively supported by one of the combination of the elevation mechanism 20 and the platform 30 when there is no patient laying on a mattress 45 of the patient bed 10, and the platform 30 alone when there is a patient 50 laying on the mattress 45 of the patient bed 10. The patient bed 10 further includes first and second docking assemblies 60, 70 respectively mounted to a bed frame 80 and the platform 30 for docking the collimator assembly 40 thereto.

The docking assemblies 60, 70 include self-aligning guide pins 90, 92 for maintaining a horizontal position of the collimator assembly 40 and its collimators therein during docking and post-docking. Even though the figures illustrate two pairs of guide pins for each docking assembly, each docking assembly can be provided with additional guide pins to better maintain the horizontal position of the collimator assembly 40.

Figure 3A:
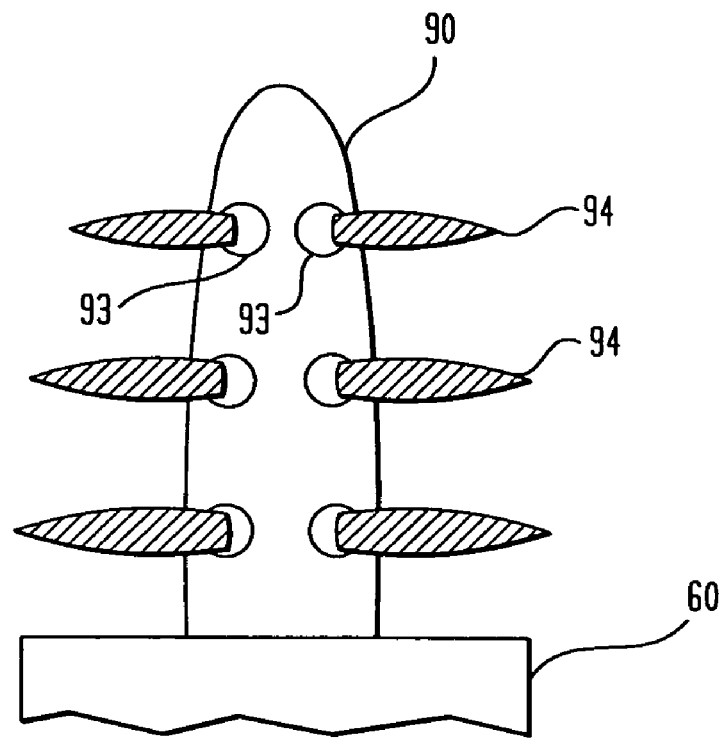
FIG. 3A is enlarged view of a guide pin of a docking assembly in accordance with an embodiment of the present invention.

As shown by FIG. 3A, the guide pins 90, 92 may include a plurality of openings 93 which enable rods 94 to protrude there from for securing the collimator assembly 40 (not shown in FIG. 3) to each of the docking assemblies 60, 70 for locking the collimator assembly 40 to the bed frame 80 and the platform 30. The rods 94 are controlled either manually or automatically by a control panel (not shown). Preferably, the first docking assembly 60 includes a combination of electrical and mechanical mechanisms for providing a redundancy to reduce the risk of the collimator assembly 40 falling from the bed frame 80. These could include electrical interlocks and electromechanical latches, as well as motion control software checks either in combination or individually as needed to provide a fail-safe operation.

Figure 3B:
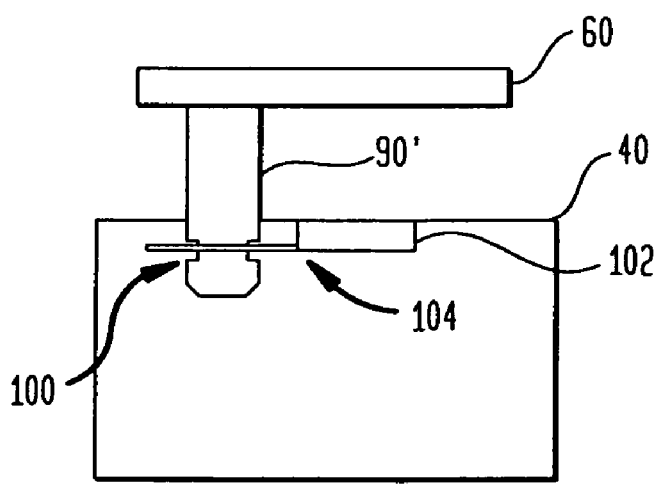
FIG. 3B is a cross-sectional view of an alternative guide pin of the docking assembly in accordance with an embodiment of the present invention.

As shown by FIG. 3B, an alternative guide pin 90' includes a collar 100 for receiving and interlocking with a slide 102 of a slide assembly 104. The slide assembly 104 is included within the collimator assembly 40 and can be manually or automatically controlled for sliding the slide 102 in a transverse direction for interlocking and un-interlocking with the collar 100 of the guide pin 90'.

Figure 3C:
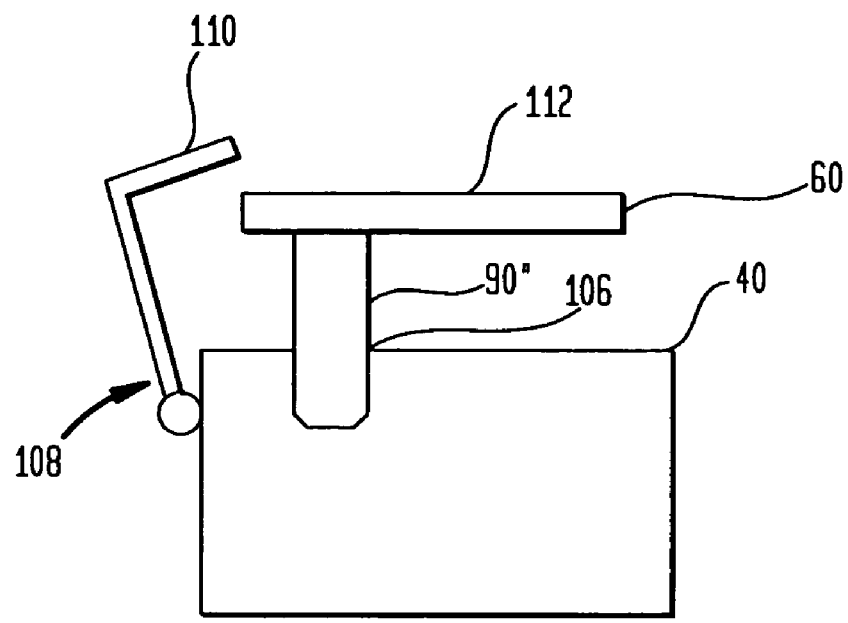
FIG. 3C is a cross-sectional view of still another alternative guide pin of the docking assembly in accordance with an embodiment of the present invention.

As shown by FIG. 3C, a guide pin 90″ is received within an opening 106 of the collimator assembly 40 and a locking assembly 108 having an L-shaped locking bar 110 is pivoted towards the docking assembly 60 (or 70). The L-shaped locking bar 110 wedges against a surface 112 of the docking assembly 60 to secure the collimator assembly 40 to the docking assembly 60.

Figure 3D:
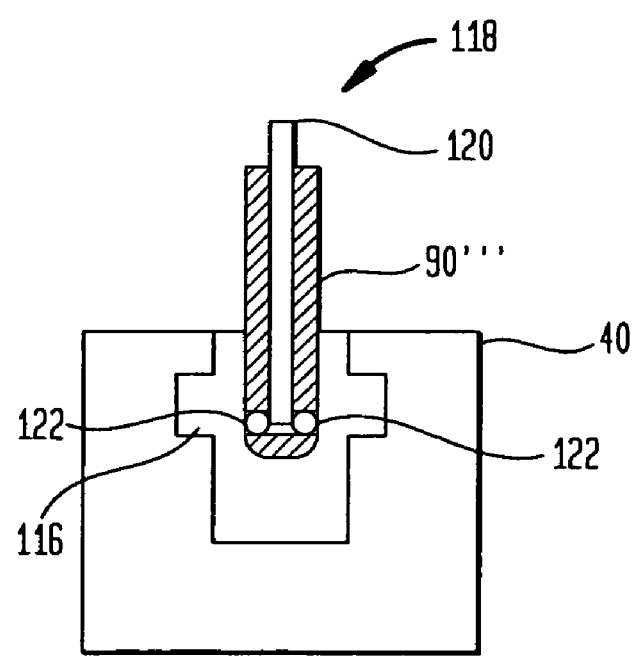
FIG. 3D is a cross-sectional view of a further alternative guide pin of the docking assembly in accordance with an embodiment of the present invention.

As shown by FIG. 3D, a guide pin 90‴ is received within a cavity 114 of the collimator assembly 40. The cavity 114 includes a circular collar 116. The guide pin 90‴ is provided with a locking assembly 118 having a guide rod 120 and a pair of ball bearings 122 configured for being received within the circular collar 116 when the guide rod 120 is pushed in the direction shown by the arrow. When the ball bearings 122 are received within the circular collar 116, the collimator assembly 40 is secured or locked to the docking assembly 60 (or 70). To unlock the collimator assembly 40 the guide rod 122 is moved in the direction opposite the arrow which causes the ball bearings 122 to disengage from the collar 116.

The bed frame 80 is operatively connected to the elevation mechanism 20 for raising and lowering the bed frame 80 with respect to the platform 30. The elevation mechanism 20 is fixed to the platform 30 of the patient bed 10 and includes supports, bearings and motors for raising and lowering the bed frame 80. The components of the elevation mechanism 20 are adapted to support the weight of the patient 50 laying on the mattress 45 during an examination procedure or other medical procedure. When the patient 50 is laying on the mattress 45, the collimator assembly 40 is docked to the second docking assembly 70. The components of the elevation mechanism 20 are also adapted to support the weight of the collimator assembly 40 and the full compliment of collimators within the collimator assembly 40 when there is no patient laying on the mattress 45.

Hence, the weight required to be supported by the elevation mechanism 20 of the patient bed 10 is less than the weight required to be supported by an elevation mechanism of a prior art patient bed. The elevation mechanism of the prior art patient bed is required to support the weight of the patient laying on the mattress and the collimator assembly.

During operation of the patient bed 10, when the collimator trays within the collimator assembly 40 must be changed, the patient 50 is removed and the bed frame 80 is moved downward by operating the elevation mechanism 20 for docking the collimator assembly 40 to the first docking assembly 60. The self-aligning guide pins 90 are inserted within openings of the collimator assembly 40 and the rods 94 are allowed to protrude from the guide pins 90 to lock the collimator assembly 40 to the first docking assembly 60. The rods 94 of guide pins 92 are then retracted to unlock the collimator assembly 40 from the platform 30. The elevation mechanism 20 is then used to raise the collimator assembly 40 and the collimator trays therein can be changed.

When the collimator trays have been changed, the elevation mechanism 20 is used to lower the collimator assembly 40 towards the platform 30 for docking the collimator assembly 40 to the second docking assembly 60. The rods 94 protruding from the guide pins 90 are then retracted for unlocking the collimator assembly 40 from the bed frame 80, and the rods 94 of the guide pins 92 are protruded for locking the collimator assembly 40 to the platform 30. If the rods 94 are protruding while the rods 94 are protruded for locking the collimator assembly 40 to the platform 30, the collimator assembly is secured to both the bed frame 80 and the platform 30.

The elevation mechanism 20 can be provided with a fail-safe mechanism which prevents the elevation mechanism 20 from operating and raising the bed frame if the fail safe mechanism detects a weight greater than a predetermined threshold weight; the predetermined threshold weight being the sum of the weight of the collimator assembly 40, mattress 45 and bed frame 80. Therefore, if a patient is laying on the mattress 45, the fail safe mechanism would detect a weight greater than the predetermined threshold weight and prevent the elevation mechanism 20 from operating and raising the collimator assembly 40.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A patient bed comprising:
   a platform;
   a bed frame;
   an elevation mechanism secured to the platform and the bed frame and operable for raising and lowering the bed frame with respect to the platform; and
   a collimator assembly configured for being selectively received by a first docking assembly secured to the platform and a second docking assembly secured to the bed frame.

2. The patient bed according to claim 1, wherein the elevation mechanism raises the collimator assembly if said collimator assembly is docked to the first docking assembly.

3. The patient bed according to claim 1, further comprising a mattress supported by the bed frame.

4. The patient bed according to claim 1, wherein the first and second docking assemblies include self-aligning guide pins for maintaining a horizontal position of the collimator assembly during docking and post-docking.

5. The patient bed according to claim 4, wherein the guide pins include a plurality of openings which enable rods to protrude there from for securing the collimator assembly to the first and second docking assemblies.

6. The patient bed according to claim 4, wherein each of the guide pins define a collar at an end thereof configured for receiving a slide of a slide assembly for securing the collimator assembly to the first and second docking assemblies.

7. The patient bed according to claim 1, further comprising a locking assembly for securing the collimator assembly to the first and second docking assemblies.

8. The patient bed according to claim 7, wherein the locking assembly includes at least one ball bearing configured for being received within a collar defined by the collimator assembly.

9. A patient bed comprising:
   a platform;
   a bed frame;
   an elevation mechanism secured to the platform and the bed frame and operable for raising and lowering the bed frame with respect to the platform;
   a first docking assembly secured to the bed frame for receiving a collimator assembly; and
   a second docking assembly secured to the platform for receiving the collimator assembly.

10. The patient bed according to claim 9, wherein the elevation mechanism raises the collimator assembly if said collimator assembly is docked to the first docking assembly.

11. The patient bed according to claim 9, further comprising a mattress supported by the bed frame.

12. The patient bed according to claim 9, wherein the first and second docking assemblies include self-aligning guide pins for maintaining a horizontal position of the collimator assembly during docking and post-docking.

13. The patient bed according to claim 12, wherein the guide pins include a plurality of openings which enable rods to protrude there from for securing the collimator assembly to the first and second docking assemblies.

14. The patient bed according to claim 12, wherein each of the guide pins define a collar at an end thereof configured for receiving a slide of a slide assembly for securing the collimator assembly to the first and second docking assemblies.

15. The patient bed according to claim 9, further comprising a locking assembly for securing the collimator assembly to the first and second docking assemblies.

16. The patient bed according to claim 15, wherein the locking assembly includes at least one ball bearing configured for being received within a collar defined by the collimator assembly.

17. A patient bed comprising:
a platform;
a bed frame;
means for raising and lowering the bed frame with respect to the platform; and
means for selectively securing a collimator assembly to at least one of the platform and the bed frame, wherein the guide pins include a plurality of openings which enable rods to protrude there from for securing the collimator assembly to the means for selectively securing.

18. The patient bed according to claim 17, further comprising a mattress supported by the bed frame.

19. The patient bed according to claim 17, wherein the means for selectively securing include self-aligning guide pins for maintaining a horizontal position of the collimator assembly during docking and post-docking.

20. The patient bed according to claim 17, wherein each of the guide pins define a collar at an end thereof configured for receiving a slide of a slide assembly for securing the collimator assembly to first and second docking assemblies secured to the platform and the bed frame, respectively.

21. The patient bed according to claim 17, further comprising a locking assembly for securing the collimator assembly to first and second docking assemblies secured to the platform and the bed frame, respectively.

22. The patient bed according to claim 21, wherein the locking assembly includes at least one ball bearing configured for being received within a collar defined by the collimator assembly.

* * * * *